(12) United States Patent
Stevens

(10) Patent No.: US 11,749,378 B2
(45) Date of Patent: Sep. 5, 2023

(54) METHODS AND DEVICES FOR NUCLEIC ACID-BASED REAL-TIME DETERMINATION OF DISEASE STATES

(71) Applicant: Noscendo GmbH, Duisburg (DE)

(72) Inventor: Philip Stevens, Alpen (DE)

(73) Assignee: Noscendo GmbH, Duisburg (DE)

(*) Notice: Subject to any disclaimer, the term of this patent is extended or adjusted under 35 U.S.C. 154(b) by 797 days.

(21) Appl. No.: 16/631,523

(22) PCT Filed: Jul. 18, 2018

(86) PCT No.: PCT/EP2018/069493
§ 371 (c)(1),
(2) Date: Jan. 16, 2020

(87) PCT Pub. No.: WO2019/016258
PCT Pub. Date: Jan. 24, 2019

(65) Prior Publication Data
US 2020/0176079 A1 Jun. 4, 2020

(30) Foreign Application Priority Data
Jul. 19, 2017 (EP) ..................................... 17182104

(51) Int. Cl.
| | |
|---|---|
| *A61B 5/00* | (2006.01) |
| *A61B 10/00* | (2006.01) |
| *C12Q 1/68* | (2018.01) |
| *C12Q 1/06* | (2006.01) |
| *C12Q 1/04* | (2006.01) |
| *G16B 30/00* | (2019.01) |
| *C12Q 1/689* | (2018.01) |
| *G16B 35/00* | (2019.01) |

(52) U.S. Cl.
CPC .............. *G16B 30/00* (2019.02); *C12Q 1/689* (2013.01); *C12Q 2535/122* (2013.01); *G16B 35/00* (2019.02)

(58) Field of Classification Search
CPC ...... A61B 1/00; C12Q 1/06; C12Q 2600/106; C12Q 2600/112; C12Q 2535/122
See application file for complete search history.

(56) References Cited

U.S. PATENT DOCUMENTS

| | | | |
|---|---|---|---|
| 9,228,232 B2 | 1/2016 | Faham et al. |
| 2013/0316331 A1 | 11/2013 | Isakov et al. |
| 2015/0105277 A1 | 4/2015 | Stewart et al. |
| 2017/0058365 A1 | 3/2017 | Locke et al. |

FOREIGN PATENT DOCUMENTS

| | | |
|---|---|---|
| JP | 2017500015 A | 1/2017 |
| RU | 2435865 C2 | 12/2011 |
| WO | 2007083147 A2 | 7/2007 |
| WO | 2015070086 A1 | 5/2015 |
| WO | 2017042287 A1 | 3/2017 |
| WO | 2019/016258 | 1/2019 |

OTHER PUBLICATIONS

P. Andersson et al., "Sequences of multiple bacterial genomes and a Chlamydia trachomatis genotype from direct sequencing of DNA derived from a vaginal swab diagnostic specimen," *Clinical Microbiology and Infectio*, vol. 19, No. 9, Sep. 1, 2013.
S. Grumaz et al., "Next-generation sequencing diagnostics of bacteremia in septic patients", *Genome Medicine*, vol. 19, No. 6, Jul. 1, 2016.
H. Hasman et al., "Rapid Whole-Genome Sequencing for Detection and Characterization of Microorganisms Directly form Clinical Samples", *Journal of Clinical Microbiology*, vol. 52, No. 1, Oct. 30, 2013.
P. Turnbaugh et al., "A core gut microbiome in obese and lean twins", *Nature*, vol. 457, No. 7228, Jan. 22, 2009.
K. Voelkerding et al., "Next-Generation Sequencing: From Basic Research to Diagnostics", *Clinical Chemistry*, vol. 55, No. 4, Feb. 26, 2009.
European Patent Office, International Search Report in International Application No. PCT/EP2018/069493 (dated Oct. 4, 2018).
European Patent Office, Written Opinion in International Application No. PCT/EP2018/069493 (dated Oct. 4, 2018).

*Primary Examiner* — Barry A Chestnut
(74) *Attorney, Agent, or Firm* — Neal, Gerber & Eisenberg LLP

(57) ABSTRACT

The present invention is directed to methods and devices for real-time diagnosis of disease states in subjects, for example, infections caused by one or more microorganisms or cancer.

15 Claims, 3 Drawing Sheets

METHODS AND DEVICES FOR NUCLEIC ACID-BASED REAL-TIME DETERMINATION OF DISEASE STATES

CROSS-REFERENCE TO RELATED APPLICATIONS

The present application is a National Stage Entry of International Application Number PCT/EP2018/069493, which was filed on Jul. 18, 2018 and claims priority benefit of European Patent Application No. 17 182 104.4 filed on Jul. 19, 2017, the contents of the aforementioned applications are incorporated herein by reference in their entirety.

FIELD OF THE INVENTION

The present invention relates to methods and devices for the determination of a disease state in a subject, such as an infection, as well as the identification of the causative agent of the disease state, which methods are based on the determination over time of the amount of nucleic acid in a subject that does not map to the subject relative to nucleic acids that map to the subject.

BACKGROUND OF THE INVENTION

Methods for the diagnosis of infectious diseases currently can be divided into two broad areas. One area relates to diagnosing an infection in relation to the host (possibly infected) organism. In this area, the diagnosis presents itself in the form of a yes or no answer to the question of whether or not the host suffers from an infection; yes an infection is present, or no an infection is not present. The other way to diagnose infection-associated diseases is to diagnose the infection causing microorganism. In this case as well, the diagnostic procedures only generate yes/no answers; yes patient X is suffering from microorganism Y or no, he/she is not.

Diagnostics that focus on identifying the disease causative microorganism are based today on either blood culture or PCR techniques. Besides the purely qualitative result (yes/no answer) those diagnostic approaches are only capable of detecting a defined set of microorganisms. For blood culture this is due to the fact that not all microorganisms can grow inside the blood culture bottle (e.g., viruses or fungi). In the case of PCR-based diagnostics, set(s) of primer pairs has to be defined which limits the specificity for an overly large set of targets, e.g., due to complexity reasons. These diagnostic tests do not enable unbiased high-specificity, high-sensitivity testing for all classes of possible microorganisms, e.g., bacteria, fungi, viruses and parasites. In addition, although PCR-based approaches are faster than blood culture, blood culture remains the first line diagnostic test for infectious diseases.

Furthermore, both approaches are not able to discriminate between commensal microorganisms, contamination, and the true infectious agent that the patient is suffering from. This ultimately leads to many false positive results.

Traditional blood culture testing takes between two to seven days. During this time, before the causative microorganism is known, patients are treated using broad spectra antibiotics, as adjudged by the treating physician following the most recent treatment guidelines. Due to this, microorganisms can become multi-resistant due to the indiscriminate overuse of broad spectra antibiotics, in view of the inferior diagnostic procedures. Thus, in order to provide fast and effective treatment of patients using appropriate anti-infective agents, it is necessary that the infectious agent be identified as fast as possible, and it is of the utmost importance to be able to discriminate between the infectious agent and commensal microorganisms/contamination during the diagnostic procedure.

There are examples in the literature of the sequencing of samples obtained from patients to identify microorganisms contained therein, such as Hasman et al., 2014, Journal of Clinical Microbiology 52:139-146, describing whole genome sequencing on urine samples to identify microorganisms contained therein, which sequence results were compared to the results obtained with conventional culturing and identification. Others include Grumaz et al., 2016, Genome Medicine 8:73, disclosing next-generation sequencing of samples obtained from septic patients; Andersson et al., 2013, Clin Microbiol Infect 19: $E_{405}$-E408, describing ultra-deep sequencing of DNA derived from a vaginal swab diagnostic specimen; and Turnbaugh et al., 2009, Nature 457:480-484, describing shotgun sequencing of total fecal DNA to identify genes commonly enriched in the obese or lean gut microbiome. These methods simply sequence and compare non-host nucleic acids to databases for identifying any microorganisms in the sample.

However, there remains a need in the art for more efficient processing of the sequence data such that more accurate results are provided and/or allows for the faster identification of the disease causing microorganism such that effective treatment can be started earlier.

SUMMARY OF THE INVENTION

The present invention is based, at least in part, on the inventors' discovery that the likelihood that a subject has a disease state can be determined in view of the amount of a nucleic acid present in a biological sample obtained from a subject, but which is not normally present in a healthy subject. For example, by determining the amount of a nucleic acid mapping to microorganism(s) in a biological sample obtained from a subject, the likelihood that the subject is suffering from a disease state, such as an infection, caused by the microorganism(s) can be determined. Also, this discovery allows for the determination of the likelihood that the subject has cancer, and is particularly useful in monitoring cancer treatment. This likelihood is, in one embodiment, determined by computing a significance score for the probability of finding in the subject a nucleic acid sequence mapping to a particular microorganism based on the total number of sequence reads mapped (assigned) to the particular microorganism and the total number of all sequence reads that can be mapped (assigned) to a species, including the number of reads mapped to the same species as the subject and the number of reads mapped to any microorganisms in the sample. This significance score, based essentially on the ratio of the number of sequence reads mapped to the particular microorganism and the total number of sequence reads mapped to a species present in a biological sample obtained from a subject, can be computed over time, i.e., computed in real time, as the total number of mapped reads increases (as more and more sequence reads are obtained and mapped to a species).

In an embodiment, the present invention is directed to a method for determining the presence of microorganisms in a subject which in one embodiment comprises determining the number of sequence reads mapping to the genome of a particular microorganism and the number of sequence reads mapping to the genome of a species, including the same species as the subject. The sequence reads, obtained from sequencing nucleic acids present in a biological sample obtained from the subject, can be compared to one or more databases comprising the genetic information from a control subject of the same species and the genetic information from a plurality of microorganisms. It follows that the number of sequence reads mapping to a species, including the host species and any microorganisms, and the number of sequence reads mapping to a particular microorganism can be determined. In an embodiment, the method further comprises calculating a significance score for a particular microorganism, which significance score is based on the number of sequence reads mapping to that particular microorganism and the total number of reads mapping to a species. Since the determining step can be carried out over time, this significance score calculation also can be performed over time as the sequence reads are being obtained and mapped. Also, this calculation can be performed over time as the sequence reads are compared to the genetic information in the one or more databases in embodiments where the sequence reads already have been obtained but not yet have been compared and mapped to a species.

The present invention is directed to a method for determining the presence of microorganisms in a subject comprising the steps of (a) sequencing nucleic acids present in a biological sample obtained from the subject to obtain a plurality of nucleic acid sequence reads; (b) comparing sequence reads obtained in step (a) with one or more databases comprising the genetic information from a control subject of the same species and the genetic information from a plurality of microorganisms to determine whether or not a compared sequence read maps to a species; and (c) determining over time the number of compared sequence reads mapping to a particular microorganism and the number of compared sequence reads mapping to a species.

The present invention is also directed to a method for determining the presence of microorganisms in a subject comprising (a) comparing sequence reads with one or more databases comprising the genetic information from a control subject of the same species and the genetic information from a plurality of microorganisms to determine whether or not a compared sequence read maps to a species, wherein the sequence reads are obtained by sequencing nucleic acids present in a biological sample obtained from the subject; and (b) determining over time the number of compared sequence reads mapping to a particular microorganism and the number of compared sequence reads mapping to a species.

The present invention is also directed to a method for determining the presence of microorganisms in a subject comprising a step of determining over time the number of compared sequence reads mapping to a particular microorganism and the number of compared sequence reads mapping to a species, wherein the compared sequence reads are obtained by comparing generated sequence reads with one or more databases comprising the genetic information from a control subject of the same species and the genetic information from a plurality of microorganisms to determine whether or not a compared sequence read maps to a species, and wherein the sequence reads are generated by sequencing nucleic acids present in a biological sample obtained from the subject.

In an embodiment of the invention, the method further comprises computing a significance score for the probability of finding in the subject a compared sequence read mapping to the particular microorganism based on the number of compared sequence reads mapping to the particular microorganism and the number of compared sequence reads mapping to a species.

The present invention is also directed to a method for determining the presence of microorganisms in a subject comprising a step of computing over time a significance score for the probability of finding in the subject a sequence read mapping to a particular microorganism based on the number of sequence reads mapping to the particular microorganism and the number of sequence reads mapping to a species, wherein the sequence reads mapping to the particular microorganism and the sequence reads mapping to a species are obtained by comparing sequence reads with one or more databases comprising the genetic information from a control subject of the same species and the genetic information from a plurality of microorganisms to determine whether or not a compared sequence read maps to a species comprised within the one or more databases, and wherein the sequence reads are generated by sequencing nucleic acids present in a biological sample obtained from the subject.

The present invention is also directed to a method for determining the presence of microorganisms in a subject comprising (a) step of determining over time the number of sequence reads mapping to a particular microorganism and the number of sequence reads mapping to a species, wherein the sequence reads are obtained by comparing sequence reads with one or more databases comprising the genetic information from a control subject of the same species and the genetic information from a plurality of microorganisms to determine whether or not a sequence read maps to a species comprised within the one or more databases, and wherein the sequence reads are generated by sequencing nucleic acids present in a biological sample obtained from the subject; and (b) computing a significance score for the probability of finding in the subject a sequence read mapping to the particular microorganism based on the number of sequence reads mapping to the particular microorganism and the number of sequence reads mapping to a species.

In multiple embodiments of the present invention, the method can be performed wherein the sequencing of the nucleic acids is immediately followed by, i.e., essentially concurrently with, comparing the sequence reads so as to map the reads to a species and calculate a significance score, or the sequencing can take place at any time earlier than the comparing/determining/calculating steps such that the results of the sequencing are stored, and the stored sequencing results then can be used to compare the sequenced reads with the one or more databases, and, e.g., allows for the calculation of the significance score.

In an embodiment, the step of determining over time the number of compared sequence reads mapping to a particular microorganism and the number of compared sequence reads mapping to a species means that the number of compared reads that can be mapped to a particular microorganism is counted and the number of compared reads that can be mapped to a species, i.e., reads not only mapping to the particular microorganism but also reads mapping to the subject, as well as mapping to any other microorganism present in the sample, is counted. Those sequence reads not able to be mapped to a species, possibly due to degradation, too short a length or are from a microorganism not present in the one or more databases, are not used in the present invention. Preferably, not all sequence reads are used in the present invention, only those that are able to be mapped to a species.

In one embodiment, when the significance score for the particular microorganism meets or exceeds a threshold value, the particular microorganism is determined to be present in the subject or when the significance score for the particular microorganism meets or exceeds a threshold value, the particular microorganism is determined to be relevant for causing a disease in the subject. In other embodiments, the more the significance score exceeds the threshold value, the higher the load of the microorganism is in the subject, which can reflect a more severe state of infection. In an embodiment, the threshold value is set in order to minimize the number of false positives and false negatives with regard to the relevance of the particular microorganism for causing a disease in the subject.

In another embodiment, when the significance score for the particular microorganism exceeds a threshold value with few sequence reads mapping to a species, the disease due to the presence of the microorganism can be considered to be severe. In the context of this embodiment, "few" refers to the fact that not all, i.e., a portion of, sequenced reads generated by sequencing the nucleic acids in the sample have been compared and mapped but where the threshold value has already been met or exceeded. The portion of reads compared and mapped can be 1%, 2%, 5%, 10%, 15%, 20%, 25%, 30%, 35%, 40%, 45%, 50%, 55%, 60%, 65%, 70%, 75%, 80%, 85%, 90% or 95% of all of the compared and mapped reads. Preferably, "few" refers to less than 50%, 45%, 40%, 35%, 30%, 25%, 20%, 15%, 10%, 5%, 2%, 1% of all of the compared and mapped reads. "Few" can also be a fixed number of reads, such as less than 100, 1,000, 10,000, or 100,000 reads.

In an embodiment, the method of the present invention can be performed over time until a point at which the information provided, such as the number of reads mapping to the subject/particular microorganism or another parameter, including that described below, allows for the determination with a level of certainty that a subject has or does not have a disease state or is or is not infected with one or more microorganisms, as well as the identity of the one or more microorganisms or of the type of cancer. Once this point has been reached, the method can be stopped since no additional information necessarily needs to be provided in order to determine the presence of microorganisms or a disease state in the subject.

The number of reads mapping to a particular microorganism and the number of reads mapping to a species over time can be used to generate a parameter over time which is useful not only in determining, e.g., whether a particular microorganism is relevant for a disease state in a subject, but also allows for the comparison of disease states (of the same cause) between two or more patients. In other words, where there is the same number of reads mapped to a species between two patients but there is a different (more or less) number of reads mapped to a particular microorganism, this difference can indicate a difference in burden/amount of the particular microorganism between the two patients. For example, if a subject has 1 read of a particular microorganism in $10^6$ reads mapped to a species and a second subject has 1 read for the same particular microorganism in $5 \times 10^5$ reads mapped to a species, it can be concluded that the microorganism is not only present in the second subject but that the second subject has a higher load/level of infection.

Moreover, this parameter can be generated in real time at any time (over time) during the method, not just at the end point where all sequence reads have been compared and where all compared reads have been mapped. Thus, if one subject is seen to have 5 times the number of reads mapped to a particular microorganism relative to the same number of reads mapped to a species as would be seen in a control sample at a time point in which only a fraction of the total reads have been compared and mapped, the method can be stopped at that earlier time point prior to comparing and mapping all sequenced reads since it is clear that the patient with 5 times more reads is likely to have a disease state (infection) due to the particular microorganism.

The ability to generate this parameter over time during the sequencing, comparing and mapping steps, such that the method can be stopped prior to the end of the analysis, i.e., in which all nucleic acids in the sample have been sequenced and all reads have been compared and mapped, advantageously allows for savings in time and resources compared to methodologies that cannot be so stopped. For example, normally the sequencing, comparing and mapping steps of all of the nucleic acids in a sample can take up to 30 hours or more. However, the present invention allows for significantly decreasing this time, for example, in some cases by 10 hours or more, such that 10 hours of sequencing and/or computer time can be saved. Moreover, since the subject can be diagnosed more quickly, appropriate treatment can be started more quickly resulting in a higher likelihood of survival for the subject. This also allows for not wasting pharmaceuticals which are not properly targeted to treating the infection or disease state, e.g., giving an antibiotic for a viral infection or giving an antibiotic for which the microorganism is resistant.

The present invention is also directed to a method for determining the presence of a disease state in a subject comprising (a) sequencing nucleic acids present in a biological sample obtained from the subject to obtain a plurality of nucleic acid sequence reads; (b) comparing sequence reads obtained in step (a) with one or more databases comprising the genetic information from a control subject of the same species to determine whether or not a compared sequence read maps to the control subject; and (c) determining over time the number of compared sequence reads mapping and not mapping to the control subject. The present invention is also directed to a method for determining the presence of a disease state in a subject comprising (a) comparing sequence reads with one or more databases comprising the genetic information from a control subject of the same species to determine whether or not a compared sequence read maps to the control subject, wherein the sequence reads are obtained by sequencing nucleic acids present in a biological sample obtained from the subject; and (b) determining over time the number of compared sequence reads mapping and not mapping to the control subject. The present invention is also directed to a method for determining the presence of a disease state in a subject comprising a step of determining over time the number of compared sequence reads mapping and not mapping to a control subject, wherein the compared sequence reads are obtained by comparing generated sequence reads with one or more databases comprising the genetic information from a control subject of the same species to determine whether or not a compared sequence read maps to the control subject, and wherein the sequence reads are generated by sequencing nucleic acids present in a biological sample obtained from the subject.

In one embodiment, the method further comprises computing a significance score for the probability of finding in the subject a compared sequence read not mapping to the control subject based on the number of compared sequence reads not mapping to the control subject and the number of compared sequence reads able to be mapped, e.g., mapping to the control subject.

The present invention is also directed to a method for determining the presence of a disease state in a subject comprising a step of computing over time a significance score for the probability of finding in the subject a sequence read not mapping to the control subject based on the number of sequence reads not mapping to the control subject and the number of sequence reads mapping to the control subject, wherein the sequence reads mapping to the control subject and the sequence reads not mapping to the control subject are obtained by comparing sequence reads with one or more databases comprising the genetic information from a control subject of the same species to determine whether or not a compared sequence read maps to the control subject, and wherein the sequence reads are generated by sequencing nucleic acids present in a biological sample obtained from the subject.

In an embodiment, when the significance score meets or exceeds a threshold value, the disease state is determined to be present in the subject. As used herein, the term "compared sequence read not mapping to the control subject", does not always mean that the sequence is not highly similar or is not practically the same as the sequence of the control subject, it often can be. For example, in an embodiment where the disease state is one which is caused by a point mutation in the nucleic acid sequence of the subject, a sequence read having such a point mutation is considered not to map to the control subject, even if all the other nucleotides of the read are identical with the control subject. Moreover, in an embodiment, when comparing the sequence reads, reference can be made to known genomic polymorphisms, e.g., single nucleotide polymorphisms, such that these differences are not considered mutations in the sequenced reads of the subject.

In an embodiment of the invention, the disease state is cancer, preferably cancer caused by a genetic abnormality, e.g., a point mutation, a deletion, an insertion or an indel. In another embodiment, the disease state is an infection caused by a microorganism, preferably wherein the microorganism is a virus, a bacterium, a fungus or a parasite.

In an embodiment where the disease state is cancer, the methods of the invention can also be used to monitor the treatment of the cancer as well as monitor for the reappearance of the cancer after a round of treatment. For example, a subject who has been diagnosed with cancer is subject to a treatment, such as surgical removal of the tumor. A database of the genetic information of the tumor can be made and nucleic acids obtained from the subject can be sequenced and reads can be compared to one or more databases containing the genetic information of a control subject from the same species and the genetic information of the tumor. The compared reads are then mapped to the control subject or to the tumor database, such that a significance score according to the invention is calculated based on the number of reads mapped to the cancer genome and the number of reads mapped to the cancer genome and the control genome, thus allowing for the determination of the presence of the cancer, i.e., the reappearance of the cancer. Similarly, samples can be obtained during treatment and the score calculated to determine if the treatment is having an effect.

In an embodiment where the disease state is an infection by a microorganism, the method of the invention also can be used to monitor the treatment of the infection and/or monitor for the reappearance of the infection. In such embodiments, biological samples are obtained from the subject during and/or after treatment and the method as described above is followed such that a significance score is calculated based on the number of reads mapping to a microorganism and the number of reads mapping to a species.

In certain embodiments, the biological sample can be selected from the group consisting of whole blood, serum, blood plasma, amniotic fluid, synovial fluid, liquor, tissue or cell smear, tissue or cell swab, urine, tissue, sputum, stool, gastrointestinal secretions, lymph fluid, and lavage.

In certain embodiments, the subject is a vertebrate, preferably a mammal, for example, human, dog, cat, pig, horse, cattle, sheep, goat, mouse, or rat, preferably the subject is human.

In an embodiment, the sequencing is carried out using ultra-deep or high-throughput sequencing methods. In preferred embodiments of the invention, the sequencing is performed by molecular high-throughput sequence analysis, i.e., by next-generation or third generation sequencing, such as by the Illumina/Solexa or the Oxford Nanopore methodology.

In an embodiment of the present invention, when the particular microorganism or the disease state is determined to be present in the subject, the method further comprises administering to the subject a pharmaceutically-active compound known to treat the disease caused by the particular microorganism or the disease state. Moreover, once the microorganism causing the infectious disease has been identified, it can be determined whether or not it is resistant to any type of antibiotics/anti-infectives, such that the treatment will be effective. In an embodiment, the nucleic acids of the subject in the sample can be depleted prior to determining whether or not the microorganism is resistant to any type of antibiotics/anti-infectives.

In one particular embodiment, the method for diagnosing an infectious disease caused by microorganism(s) in a subject comprises computing over time a significance score for the probability of finding in the subject a sequence read mapping to a particular microorganism based on the number of sequence reads mapping to the particular microorganism and the number of compared sequence reads mapping to a species, wherein when the score for the particular microorganism meets or exceeds a threshold value, the particular microorganism is determined to be causing the infectious disease, and wherein the sequence reads mapping to the particular microorganism and the sequence reads mapping to a species are obtained by comparing sequence reads with one or more databases comprising the genetic information from a control subject of the same species and the genetic information from a plurality of microorganisms to determine whether or not a compared sequence read maps to a species comprised within the one or more databases, and wherein the sequence reads are generated by sequencing nucleic acids present in a biological sample obtained from the subject.

In one particular embodiment, the method for diagnosing an infectious disease caused by microorganism(s) in a subject comprises (a) sequencing nucleic acids present in a biological sample obtained from the subject to obtain a plurality of nucleic acid sequence reads; (b) comparing sequence reads obtained in step (a) with one or more databases comprising the genetic information from a control subject of the same species and the genetic information from a plurality of microorganisms to determine whether or not a compared sequence read maps to a species comprised within the one or more databases; (c) determining over time the number of compared sequence reads mapping to a particular microorganism and the number of compared sequence reads mapping to a species; and (d) computing a significance score for the probability of finding in the subject a compared sequence read mapping to the particular microorganism based on the number of compared sequence reads mapping to the particular microorganism and the number of compared sequence reads mapping to a species, wherein when the score for the particular microorganism meets or exceeds a threshold value, the particular microorganism is determined to be causing the infectious disease.

The present invention is directed to a method of treating a disease or infection caused by a microorganism in a subject comprising (a) determining the significance score for a particular microorganism in a subject in accordance with any of the foregoing methods for determining the presence of microorganisms in a subject, and (b) when the significance for the particular microorganism meets or exceeds a threshold value, administering to the subject a compound that inhibits the growth of the particular microorganism. The present invention is also directed to a method of treating a disease or infection caused by a microorganism in a subject comprising administering to the subject a compound that inhibits the growth of a microorganism whose significance score meets or exceeds a threshold value, wherein the significance score is calculated according to any of the foregoing methods for determining the presence of microorganisms in a subject described herein.

The present invention also encompasses a computer-readable storage medium storing program code comprising instructions which when executed by a processor carry out the methods of the invention, as well as a computer system comprising a processor, e.g., a field-programmable gate array, configured to carry out the methods of the invention.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., (1995) Helvetica Chimica Acta, CH-4010 Basel, Switzerland.

The practice of the present invention will employ, unless otherwise indicated, conventional methods of biochemistry, cell biology, immunology, and recombinant DNA techniques which are explained in the literature in the field (cf., e.g., Molecular Cloning: A Laboratory Manual, 2nd Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e., the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

As described above, the present invention is based on the number of sequence reads mapping, e.g., to a particular microorganism or to a cancer genome, in relation to the total number of reads able to be mapped, e.g., to a species/normal genome. Thus, the present invention provides a foundation for diagnosing and distinguishing between commensals/contamination and the most probable infection causative agent. Advantageously, the present invention provides at least the following:

a) an unbiased method that does not make any assumption about the obtained biological sample,
b) a method which is able to discriminate between commensals/contamination and an infectious agent,
c) a method which provides results in real time for all microorganisms identified in a sample at a given time,
d) a method generating data in real time during sequencing,
e) a method providing information in real time while handling data,
f) a method that can be stopped after analyzing only a small portion of the whole dataset once a microorganism is determined to be significant/relevant to the disease state,
g) a method which generates a parameter that allows for comparing two or more biological samples of the same disease state, and h) a method which enables clinicians and researchers to compare the degree of severity of an infection due to a microorganism among patients infected with the same microorganism.

Another advantage of the present invention is the ability to detect infections caused by multiple microorganisms, and the ability to determine which microorganism is the main causative agent and which are accompanying agents even though all may be contributing significantly to the state of infection/illness.

The terms "subject", "individual", "organism" or "patient" are used interchangeably and relate to vertebrates, preferably mammals. For example, mammals in the context of the present invention are humans, non-human primates, domesticated animals such as dogs, cats, sheep, cattle, goats, pigs, horses etc., laboratory animals such as mice, rats, rabbits, fish, guinea pigs, etc. as well as animals in captivity such as animals of zoos. The tem "animal" also includes humans. Preferably, the terms "subject", "individual", "organism" or "patient" refer to male and female mammals, in particular male and female humans. The subject can be of any age, including neonates (e.g., from birth to about 6 months), infants (e.g., from about 6 months to about 2 years), children (e.g., from about 2 years to about 10 years), adolescents (e.g., from about 10 years to about 21 years), and adults (e.g., about 21 years and older).

In certain embodiments, the subject can be immunocompromised, e.g., due to taking immunosuppressive drugs or is undergoing a transplant requiring the suppression or destruction of the native immune system/function. Other subjects can be those with chronic or systematic infections. In specific embodiments, the subject may be suspected of or suffering from sepsis, endocarditis, infection of a joint, including artificial joints, or soft-tissue infection. In an embodiment, the subject is a newborn suspected of having or having sepsis. In another embodiment, the suspected infection is in the uterus, e.g., an intra-amniotic infection (chorioamnionitis), during pregnancy.

In the context of the present invention, a "control" or "control group" refers to a biological sample from a subject or samples from a group of subjects, respectively, that are healthy or considered to be healthy, i.e., not suffering from a disease or at least not suffering from the same disease as the subject being tested. Preferably, the control or control group comprises sample(s) from healthy individuals that match the subject in a variety of ways, for example, similar age, same sex or gender, the same social class or the same ethnic group, or living in substantially the same area of a country, state, or city.

In the context of the present invention, the term "healthy" is meant to refer to subjects which do not display any signs of a particular disease, and preferably which are not currently developing the disease. For example, a healthy subject shows no signs of infection or disease, but is nonetheless a host to a variety of commensal microorganism species. Preferably, the subject is not one who is infected but at a stage of the infection where the infection is not evident.

As used herein, "biological sample" includes any biological sample obtained from a subject, e.g., from the body of the subject. Examples of such biological samples include whole blood, blood fractions such as plasma, serum, smears or swabs of a tissue, sputum, bronchial aspirate, urine, semen, stool, bile, gastrointestinal secretions, reproductive system secretions, amniotic fluid, synovial fluid, lymph fluid, liquor, bone marrow, organ aspirates and tissue biopsies, including punch biopsies. Optionally, the biological sample can be obtained from a mucous membrane of the patient. The term "biological sample" can also include processed biological samples such as fractions or isolates, e.g., nucleic acids or isolated cells. Preferably, the biological sample contains nucleic acids, e.g., genomic DNA or mRNA, such that the sequence of the nucleic acids can be determined. In an embodiment, the biological sample can be one that is obtained from a tissue showing signs of a disease state, e.g., showing signs of infection. In a preferred embodiment, the biological sample is blood or blood plasma obtained from the subject. The sample is analyzed according to the methods of the invention and during the method or thereafter is not normally returned to the body. In most embodiments, the presence of the subject's body is not necessary in order to carry out the methods of the invention.

In one embodiment, the biological sample is blood plasma, preferably obtained directly from the subject. The blood plasma is preferably cell-free, preferably mainly/mostly cell-free, e.g., fewer than 10,000, 1,000, 100, or 10 cells per mL. The biological sample, e.g., blood plasma, may contain free circulating nucleic acids, comprising nucleic acids of the subject and nucleic acids not of the subject, e.g., those of a microorganism. In one embodiment the biological sample can be diluted or concentrated. In another embodiment the sample is processed prior to sequencing, preferably the sample is purified to remove cellular components, such as lipids and proteins, prior to sequencing. In one embodiment, the biological sample is processed prior to sequencing such that only cell-free nucleic acids are sequenced.

Tissues of the patient from which the biological sample can be obtained include, but are not limited to, throat, mouth, nasal, stomach, intestinal, skin, joint, liver, pancreatic, lung, neuronal cervical, vaginal, uteral, urethral, rectal, penial, and muscle. Any suitable method for obtaining the biological sample from the patient and/or from an appropriate tissue can be used in connection with the present invention.

The term "in vivo" relates to the situation in a subject.

The term "genome" relates to the total amount of genetic information in the chromosomes of an organism or a cell.

The term "exome" refers to part of the genome of an organism formed by exons, which are coding portions of expressed genes. The exome provides the genetic blueprint used in the synthesis of proteins and other functional gene products. It is the most functionally relevant part of the genome and, therefore, it is most likely to contribute to the phenotype of an organism. The exome of the human genome is estimated to comprise 1.5% of the total genome (Ng et al., 2008, PLoS Gen 4 (8):1-15).

The term "transcriptome" relates to the set of all RNA molecules, including mRNA, rRNA, tRNA, and other non-coding RNA produced in one cell or a population of cells. In context of the present invention the transcriptome means the set of all RNA molecules produced in one cell, a population of cells, or all cells of a given individual at a certain time point.

The term "genetic material" includes isolated nucleic acid, either DNA or RNA, a section of a double helix, a section of a chromosome, or an organism's or cell's entire genome, in particular its exome or transcriptome.

According to the invention, "nucleic acid" is preferably deoxyribonucleic acid (DNA) or ribonucleic acid (RNA). Nucleic acids include genomic DNA, cDNA, mRNA, recombinantly produced and chemically synthesized molecules. A nucleic acid may be present as a single-stranded or double-stranded and linear or covalently circularly closed molecule, as well as mixtures thereof. A nucleic acid can be isolated. Preferably, the nucleic acid is a free circulating DNA and/or RNA molecule. In one embodiment, the term "nucleic acid" is also understood to mean "nucleic acid sequence". Further, prior to sequencing, the nucleic acids can be processed, for example, enriched or amplified. In cases where the nucleic acid obtained from the sample is RNA, the RNA can be reverse transcribed into DNA for sequencing or the RNA itself can be sequenced.

The term "mutation" refers to a change of or difference in the nucleic acid sequence (nucleotide substitution, addition or deletion) compared to a reference. A "somatic mutation" can occur in any of the cells of the body except the germ cells (sperm and egg) and therefore are not passed on to children. These alterations can (but do not always) cause cancer or other diseases. Preferably a mutation is a non-synonymous mutation. The term "non-synonymous mutation" refers to a mutation, preferably a nucleotide substitution, which does result in an amino acid change such as an amino acid substitution in the translation product.

According to the invention, the term "mutation" includes point mutations, indels, fusions, chromothripsis and RNA edits.

According to the invention, the term "indel" describes a special mutation class, defined as a mutation resulting in a co-localized insertion and deletion and a net gain or loss in nucleotides. In coding regions of the genome, unless the length of an indel is a multiple of 3, they produce a frameshift mutation. Indels can be contrasted with a point mutation; where an indel inserts and deletes nucleotides from a sequence, a point mutation is a form of substitution that replaces one of the nucleotides.

According to the invention, the term "chromothripsis" refers to a genetic phenomenon by which specific regions of the genome are shattered and then stitched together via a single devastating event.

Fusions can generate hybrid genes formed from two previously separate genes. It can occur as the result of a translocation, interstitial deletion, or chromosomal inversion. Often, fusion genes are oncogenes. Oncogenic fusion genes may lead to a gene product with a new or different function from the two fusion partners. Alternatively, a proto-oncogene is fused to a strong promoter, and thereby the oncogenic function is set to function by an upregulation caused by the strong promoter of the upstream fusion partner. Oncogenic fusion transcripts may also be caused by trans-splicing or read-through events.

In context of the present invention, the term "sequencing" means to determine the sequence of at least one nucleic acid, and it includes any method that is used to determine the order of the bases in a strand of at least one nucleic acid. A preferred method of sequencing is high-throughput sequencing, such as next-generation sequencing or third generation sequencing.

For clarification purposes: the terms "Next Generation Sequencing" or "NGS" in the context of the present invention mean all high throughput sequencing technologies which, in contrast to the "conventional" sequencing methodology known as Sanger chemistry, read nucleic acid templates randomly in parallel along the entire genome by breaking the entire genome into small pieces. Such NGS technologies (also known as massively parallel sequencing technologies) are able to deliver nucleic acid sequence information of a whole genome, exome, transcriptome (all transcribed sequences of a genome) or methylome (all methylated sequences of a genome) in very short time periods, e.g., within 1-2 weeks, preferably within 1-7 days or most preferably within less than 24 hours and allow, in principle, single cell sequencing approaches. Multiple NGS platforms which are commercially available or which are mentioned in the literature can be used in the context of the present invention, e.g., those described in detail in Zhang et al., 2011, The impact of next-generation sequencing on genomics. J. Genet Genomics 38:95-109; or in Voelkerding et al., 2009, Next generation sequencing: From basic research to diagnostics, Clinical chemistry 55:641-658. Non-limiting examples of such NGS technologies/platforms are 1) The sequencing-by-synthesis technology known as pyrosequencing implemented, e.g., in the GS-FLX 454 Genome Sequencer™ of Roche-associated company 454 Life Sciences (Branford, Connecticut), first described in Ronaghi et al., 1998, A sequencing method based on real-time pyrophosphate, Science 281:363-365. This technology uses an emulsion PCR in which single-stranded DNA binding beads are encapsulated by vigorous vortexing into aqueous micelles containing PCR reactants surrounded by oil for emulsion PCR amplification. During the pyrosequencing process, light emitted from phosphate molecules during nucleotide incorporation is recorded as the polymerase synthesizes the DNA strand.

2) The sequencing-by-synthesis approaches developed by Solexa (now part of Illumina Inc., San Diego, Calif.) which is based on reversible dye-terminators and implemented, e.g., in the Illumina/Solexa Genome Analyzer™ and in the Illumina HiSeq 2000 Genome Analyzer™. In this technology, all four nucleotides are added simultaneously into oligo-primed cluster fragments in flow-cell channels along with DNA polymerase. Bridge amplification extends cluster strands with all four fluorescently labeled nucleotides for sequencing.

3) Sequencing-by-ligation approaches, e.g., implemented in the SOLid™ platform of Applied Biosystems (now Life Technologies Corporation, Carlsbad, Calif.). In this technology, a pool of all possible oligonucleotides of a fixed length are labeled according to the sequenced position. Oligonucleotides are annealed and ligated; the preferential ligation by DNA ligase for matching sequences results in a signal informative of the nucleotide at that position. Before sequencing, the DNA is amplified by emulsion PCR. The resulting bead, each containing only copies of the same DNA molecule, are deposited on a glass slide. As a second example, the Polonator™ G.007 platform of Dover Systems (Salem, N.H.) also employs a sequencing-by-ligation approach by using a randomly arrayed, bead-based, emulsion PCR to amplify DNA fragments for parallel sequencing.

4) Single-molecule sequencing technologies such as, e.g., implemented in the PacBio RS system of Pacific Biosciences (Menlo Park, Calif.) or in the HeliScope™ platform of Helicos Biosciences (Cambridge, Mass.). The distinct characteristic of this technology is its ability to sequence single DNA or RNA molecules without amplification, defined as Single-Molecule Real Time (SMRT) DNA sequencing. For example, HeliScope uses a highly sensitive fluorescence detection system to directly detect each nucleotide as it is synthesized. A similar approach based on fluorescence resonance energy transfer (FRET) has been developed from Visigen Biotechnology (Houston, Tex.). Other fluorescence-based single-molecule techniques are from U.S. Genomics (GeneEngine™) and Genovoxx (AnyGene™)

5) Nano-technologies for single-molecule sequencing in which various nanostructures are used which are, e.g., arranged on a chip to monitor the movement of a polymerase molecule on a single strand during replication. Non-limiting examples for approaches based on nano-technologies are the GridON™ platform of Oxford Nanopore Technologies (Oxford, UK), the hybridization-assisted nano-pore sequencing (HANS™) platforms developed by Nabsys (Providence, R.I.), and the proprietary ligase-based DNA sequencing platform with DNA nanoball (DNB) technology called combinatorial probe-anchor ligation (cPAL™)

6) Electron microscopy based technologies for single-molecule sequencing, e.g., those developed by Light-Speed Genomics (Sunnyvale, Calif.) and Halcyon Molecular (Redwood City, Calif.)

7) Ion semiconductor sequencing which is based on the detection of hydrogen ions that are released during the polymerization of DNA. For example, Ion Torrent Systems (San Francisco, Calif.) uses a high-density array of micro-machined wells to perform this biochemical process in a massively parallel way. Each well holds a different DNA template. Beneath the wells is an ion-sensitive layer and beneath that a proprietary Ion sensor.

Other sequencing methods useful in the context of the invention include tunneling currents sequencing (Xu et al., 2007, The electronic properties of DNA bases, Small 3:1539-1543, Di Ventra, 2013, Fast DNA sequencing by electrical means inches closer, Nanotechnology 24:342501). Particularly preferable next-generation sequencing (NGS) methodologies include Illumina, IONTorrent and NanoPore sequencing.

Preferably, DNA and RNA preparations serve as starting material for NGS. Such nucleic acids can be easily obtained from biological samples, e.g., from blood or fresh, flash-frozen or formalin-fixed tissue samples or from freshly isolated cells or from circulating tumor cells (CTCs) which are present in the peripheral blood of patients. Normal (non-mutated) genomic DNA or RNA can be extracted from normal, somatic tissue, however germline cells are preferred. Germline DNA or RNA can be extracted from peripheral blood mononuclear cells (PBMCs) in patients with non-hematological malignancies. Although nucleic acids extracted can be highly fragmented, they are nonetheless suitable for NGS applications.

Several targeted NGS methods for exome sequencing are described in the literature (for review see, e.g., Teer and Mullikin, 2010, Human Mol Genet 19: R145-51), all of which can be used in conjunction with the present invention. Many of these methods (described, e.g., as genome capture, genome partitioning, genome enrichment, etc.) use hybridization techniques and include array-based (e.g., Hodges et al., 2007, Nat Genet 39:1522-1527) and liquid-based (e.g., Choi et al., 2009, Proc Natl Acad Sci USA 106:19096-19101) hybridization approaches. Commercial kits for DNA sample preparation and subsequent exome capture are also available: for example, Illumina Inc. (San Diego, Calif.) offers the TruSeq™ DNA Sample Preparation Kit and the Exome Enrichment Kit TruSeq™ Exome Enrichment Kit.

Once the nucleic acids have been sequenced, the resulting sequences (sequenced reads) can be compared to one or more databases comprising the genetic information preferably from multiple species, such that the sequenced reads can be determined to be from a particular species, such as the subject and/or from a particular microorganism, which allows for the determining the number of sequenced reads mapping to a particular microorganism and the number of sequenced reads mapping to a species, i.e., mapping to the subject as well as mapping to any microorganism. As explained above, sequenced reads which cannot be mapped to any species are not used in the present invention. Methods for mapping sequenced reads to provide information on their species of origin are well known in the art, and any such suitable method can be used in connection with the present invention. For example, the Kraken ultrafast metagenomics sequence classification methodology described in Wood and Salzberg, 2014, Genome Biol 15: R46 can be used. Another exemplary method is NextGenMap which is described in Sedlazeck et al., 2013, Bioinfonnatics 29:2790-2791. Yet another exemplary method is a cloud-compatible bioinformatics pipeline for ultra-rapid pathogen identification from next-generation sequencing of clinical samples as described in Naccache et al., 2014, Genome Res 24:1180-1192. Addition methods known in the art and useful in the present invention include, but are not limited to those described in Huson et al., 2007, Genome Res 17:377-386; Freitas et al., 2015, Nucl Acids Res 43:e69; and Kim et al., 2016, Genome Res 26:1721-1729.

In certain embodiments of the invention, in order to reduce the number of false positive findings in detecting and comparing sequences, it is preferred to determine/compare the sequences in replicates. Thus, it is preferred that nucleic acid sequences in a biological sample be determined twice, three times or more. In one embodiment, the nucleic acid sequences of a tumor sample is determined twice, three times or more. It may also be possible to determine the sequence more than once by determining at least once the sequence in genomic DNA and determining at least once the sequence in RNA of said sample. For example, by determining the variations between replicates of a sample, the expected rate of false positive (FDR) mutations as a statistical quantity can be estimated. Technical repeats of a sample should generate identical results and any detected mutation in this "same vs. same comparison" is a false positive. Furthermore, various quality related metrics (e.g., coverage or SNP quality) may be combined into a single quality score using a machine learning approach. For a given somatic variation all other variations with an exceeding quality score may be counted, which enables a ranking of all variations in a dataset.

In context of the present invention, the term "database" can relate to an organized collection of data, preferably as an electronic filing system, as well as to non-structured collections of data, such as a data lake which is a system or repository of data stored in its natural format. A data lake can be a single store of all enterprise data including raw copies of source system data and transformed data used for tasks such as reporting, visualization, analytics and machine learning.

In some embodiments, a data lake can include structured data from relational databases (rows and columns), semi-structured data (CSV, logs, XML, JSON), unstructured data (emails, documents, PDFs), and/or binary data (images, audio, video). In an embodiment, a sequence database is a type of database that is composed of a collection of computerized ("digital") nucleic acid sequences, protein sequences, or other polymer sequences stored on a computer. Preferably, the database is a collection of nucleic acid sequences, i.e., the genetic information from a number of species. The genetic information can be derived from the genome and/or the exome and/or the transcriptome of a species. Exemplary nucleic acid databases useful in the present invention include, but are not limited to, International Nucleotide Sequence Database (INSD), DNA Data Bank of Japan (National Institute of Genetics), EMBL (European Bioinformatics Institute), GenBank (National Center for Biotechnology Information), Bioinformatic Harvester, Gene Disease Database, SNPedia, CAMERA Resource for microbial genomics and metagenomics, EcoCyc (a database that describes the genome and the biochemical machinery of the model organism *E. coli* K-12), Ensembl (provides automatic annotation databases for human, mouse, other vertebrate and eukaryote genomes) Ensembl Genomes (provides genome-scale data for bacteria, protists, fungi, plants and invertebrate metazoa, through a unified set of interactive and programmatic interfaces (using the Ensembl software platform)), Exome Aggregation Consortium (ExAC) (exome sequencing data from a wide variety of large-scale sequencing projects (Broad Institute)), PATRIC (PathoSystems Resource Integration Center), MGI Mouse Genome (Jackson Laboratory), JGI Genomes of the DOE-Joint Genome Institute (provides databases of many eukaryote and microbial genomes), National Microbial Pathogen Data Resource (a manually curated database of annotated genome data for the pathogens *Campylobacter, Chlamydia, Chlamydophila, Haemophilus, Listeria, Mycoplasma, Neisseria, Staphylococcus, Streptococcus, Treponema, Ureaplasma* and *Vibrio*), RegulonDB (a model of the complex regulation of transcription initiation or regulatory network of the cell *E. coli* K-12), Saccharomyces Genome Database (genome of the yeast model organism), Viral Bioinfonnatics Resource Center (curated database containing annotated genome data for eleven virus families), The SEED platform (includes all complete microbial genomes, and most partial genomes, the platform is used to annotate microbial genomes using subsystems), WormBase ParaSite (parasitic species), UCSC Malaria Genome Browser (genome of malaria causing species (*Plasmodium falciparum* and others)), Rat Genome Database (genomic and phenotype data for *Rattus norvegicus*), INTEGRALL (database dedicated to integrons, bacterial genetic elements involved in the antibiotic resistance), VectorBase (NIAID Bioinformatics Resource Center for Invertebrate Vectors of Human Pathogens), EzGenome, comprehensive information about manually curated genome projects of prokaryotes (archaea and bacteria), GeneDB (Apicomplexan Protozoa, Kinetoplastid Protozoa, Parasitic Helminths, Parasite Vectors as well as several bacteria and viruses), EuPathDB (eukaryotic pathogen database resources includes amoeba, fungi, plasmodium, trypanosomatids etc.); The 1000 Genomes Project (providing the genomes of more than a thousand anonymous participants from a number of different ethnic groups), Personal Genome Project (providing human genomes).

Other databases can include personalized databases, such as databases comprising the genetic information of healthy and diseased tissues of the same subject. Such databases can be useful, for example, in the methods for screening for the reappearance of cancer after treatment or for monitoring the effectiveness of a treatment in a subject.

In context of the present invention, the terms "sequence read" or "read" are used interchangeably and refer to a specific nucleic acid of any size for which the nucleotide sequence has been determined by sequencing, and which is preferably assigned to a species, preferably mapped to the genome of the respective species. In a preferred embodiment, the reads are classified to a specific species, such as the subject and/or microorganisms, preferably classified to specific microorganisms. In an embodiment, reads can be normalized by their abundance.

The present invention in a further embodiment relates to a method for diagnosis of a disease state or a disease, e.g., infectious disease, in a subject, wherein a method for determining a disease state or disease in said subject according to the present invention is carried out.

In an embodiment, the invention provides a method for monitoring the infection status of a subject, preferably for monitoring a subject during treatment and response to therapy, wherein a method for determining the infection status of said subject according to the present invention is carried out.

Such methods preferably relate to the identification of a subject suffering from a disease, preferably to a screening for a disease, preferably to a preventive medical analysis. In a preferred embodiment such methods identify correlation of the occurrence of a microorganism and the development of a disease in a subject.

The present invention preferably relates to a method, wherein the pathogenic condition is characterized by abnormal, especially pathogenic quantities of nucleic acids of at least one microorganism, e.g., at least one viral, bacterial, fungal or parasitic organism.

Any microorganism, preferably one whose nucleic acid sequence is known, can be determined to be present in a subject, as well as be determined as the causative agent of a disease in the subject. Exemplary microorganisms, the presence of which that can be determined in a subject, include viruses, bacteria, fungi and parasites. Exemplary bacteria include, but are not limited to, *Neisseria meningitis Streptococcus pneumoniae, Streptococcus pyogenes, Moraxella catarrhalis, Bordetella pertussis, Staphylococcus aureus, Clostridium tetani, Corynebacterium diphtheria, Haemophilus influenza, Pseudomonas aeruginosa, Streptococcus agalactiae, Chlamydia trachomatis, Chlamydia pneumoniae, Helicobacter pylori, Escherichia coli, Bacillus anthracis, Yersinia pestis, Staphylococcus epidermis, Clostridium perfringens, Clostridium botulinum, Legionella pneumophila, Coxiella burnetii, Brucella* spp. such as *B. abortus, B. canis, B. melitensis, B. neotomae, B. ovis, B. suis, B. pinnipediae, Francisella* spp. such as *F. novicida, F. philomiragia, F. tularensis, Neisseria gonorrhoeae, Treponema pallidum, Haemophilus ducreyi, Enterococcus faecalis, Enterococcus faecium, Staphylococcus saprophyticus, Yersinia enterocolitica, Mycobacterium tuberculosis, Rickettsia* spp., *Listeria monocytogenes, Vibrio cholera, Salmonella typhi, Borrelia burgdorferi, Porphyromonas gingivalis, Klebsiella* spp., *Klebsiella pneumoniae*.

Exemplary viruses include, but are not limited to, Orthomyxoviridae, such as influenza A, B or C virus; Paramyxoviridae viruses, such as Pneumoviruses (e.g., respiratory syncytial virus, RSV), Rubulaviruses (e.g., mumps virus), Paramyxoviruses (e.g., parainfluenza virus), Metapneumoviruses and Morbilliviruses (e.g., measles); Poxviridae, such as Orthopoxvirus (e.g., Variola vera, including Variola major and Variola minor); Picornaviridae, such as Enteroviruses (e.g., poliovirus e.g. a type 1, type 2 and/or type 3 poliovirus, EV71 enterovirus, coxsackie A or B virus), Rhinoviruses, Heparnavirus, Cardioviruses and Aphthoviruses; Bunyaviruses, such as Orthobunyavirus (e.g., California encephalitis virus), Phlebovirus (e.g., Rift Valley Fever virus), or Neurovirus (e.g., Crimean-Congo hemorrhagic fever virus); Heparnaviruses (e.g., hepatitis A virus (HAV), B and C); Filoviridae (e.g., Ebola virus (including a Zaire, Ivory Coast, Reston or Sudan ebolavirus) or Marburg virus); Togaviruses (e.g., Rubivirus, Alphavirus, and Arterivirus, including rubella virus); Flaviviruses (e.g., Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, and Powassan encephalitis virus); Pestiviruses (e.g., Bovine viral diarrhea (BVDV), Classical swine fever (CSFV) and Border disease (BDV)); Hepadnavirus (e.g., Hepatitis B virus, hepatitis C virus, delta hepatitis virus, hepatitis E virus, or hepatitis G virus); Rhabdoviruses (e.g., Lyssavirus, Rabies virus and Vesiculovirus (VSV)); Caliciviridae (e.g., Norwalk virus (Norovirus), and Norwalk-like Viruses, such as Hawaii Virus and Snow Mountain Virus); Coronavirus (e.g., SARS coronavirus, avian infectious bronchitis (IBV), Mouse hepatitis virus (MHV), and Porcine transmissible gastroenteritis virus (TGEV)); Retroviruses (e.g., Oncovirus, Lentivirus (e.g. HIV-1 or HIV-2) or a Spumavirus); Reoviruses (e.g., Orthoreovirus, Rotavirus, Orbivirus, and Coltivirus); Parvoviruses (e.g., Parvovirus B19); Herpesviruses (e.g., human herpesvirus, such as Herpes Simplex Viruses (HSV), e.g., HSV types 1 and 2, Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8)); Papovaviridae (e.g., Papillomaviruses and Polyomaviruses, e.g., serotypes 1, 2, 4, 5, 6, 8, 11, 13, 16, 18, 31, 33, 35, 39, 41, 42, 47, 51, 57, 58, 63 or 65, preferably from one or more of serotypes 6, 11, 16 and/or 18); Adenoviruses, such as adenovirus serotype 36 (Ad-36).

Exemplary fungi include, but are not limited to, *Dermatophytres*, including *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton naegnini, Trichophyton mentagrophytes, Trichophyton quinckeanum, Trichophyton rubrum, Trichophyton schoenleini, Trichophyton tonsurans, Trichophyton verrucosum, T. verrucosumvar. album, var. discoides, var. ochraceum, Trichophyton violaceum*, and/or *Trichophyton faviforme; Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Microsporidia, Encephalitozoon* spp., *Septata intestinalis* and *Enterocytozoon bieneusi; Brachiola* spp., *Microsporidium* spp., *Nosema* spp., *Pleistophora* spp., *Trachipleistophora* spp., *Vittaforma* spp., *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp., *Mucor* spp., *Absidia* spp., *Mortierella* spp., *Cunninghamella* spp., *Saksenaea* spp., *Alternaria* spp., *Curvularia* spp., *Helminthosporium* spp., *Fusarium* spp., *Aspergillus* spp., *Penicillium* spp., *Monolinia* spp., *Rhizoctonia* spp., *Paecilomyces* spp., *Pithomyces* spp., and *Cladosporium* spp.

Exemplary parasites include, but are not limited to, *Plasmodium*, such as *P. falciparum, P. vivax, P. malariae* and *P. ovale*, as well as those parasites from the Caligidae family, particularly those from the Lepeophtheirus and Caligusgenera, e.g., sea lice such as *Lepeophtheirus salmonis* and *Caligus rogercresseyi*.

In context of the present invention, the term "antibiotic resistance" means a loss of susceptibility of bacteria to the killing, or growth-inhibiting properties of an antibiotic agent. It also relates to resistance of a microorganism to an antimicrobial drug that was originally effective for treatment of infections caused by it. Resistant microorganisms, including bacteria, fungi, viruses and parasites, are able to withstand attack by antimicrobial drugs, such as antibacterial drugs, antifungals, antivirals, and anti-malarials, so that standard treatments become ineffective and infections persist.

According to the invention, the term "tumor" or "tumor disease" refers to an abnormal growth of cells (called neoplastic cells, tumorigenous cells or tumor cells) preferably forming a swelling or lesion. By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant.

Cancer (medical term: malignant neoplasm) is a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor but some, like leukemia, do not. Malignancy, malignant neoplasm, and malignant tumor are essentially synonymous with cancer.

Neoplasm is an abnormal mass of tissue as a result of neoplasia. Neoplasia (new growth in Greek) is the abnormal proliferation of cells. The growth of the cells exceeds, and is uncoordinated with that of the normal tissues around it. The growth persists in the same excessive manner even after cessation of the stimuli. It usually causes a lump or tumor. Neoplasms may be benign, pre-malignant or malignant.

"Growth of a tumor" or "tumor growth" according to the invention relates to the tendency of a tumor to increase its size and/or to the tendency of tumor cells to proliferate.

For purposes of the present invention, the terms "cancer" and "cancer disease" are used interchangeably with the terms "tumor" and "tumor disease".

Cancers are classified by the type of cell that resembles the tumor and, therefore, the tissue presumed to be the origin of the tumor. These are the histology and the location, respectively.

The term "cancer" according to the invention comprises carcinomas, adenocarcinomas, blastomas, leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the invention also comprises cancer metastases and relapse of cancer.

According to the invention, a "carcinoma" is a malignant tumor derived from epithelial cells. This group represents the most common cancers, including the common forms of breast, prostate, lung and colon cancer. "Adenocarcinoma" is a cancer that originates in glandular tissue. This tissue is also part of a larger tissue category known as epithelial tissue. Epithelial tissue includes skin, glands and a variety of other tissue that lines the cavities and organs of the body. Epithelium is derived embryologically from ectoderm, endoderm and mesoderm. To be classified as adenocarcinoma, the cells do not necessarily need to be part of a gland, as long as they have secretory properties. This form of carcinoma can occur in some higher mammals, including humans. Well differentiated adenocarcinomas tend to resemble the glandular tissue that they are derived from, while poorly differentiated may not. By staining the cells from a biopsy, a pathologist will determine whether the tumor is an adenocarcinoma or some other type of cancer. Adenocarcinomas can arise in many tissues of the body due to the ubiquitous nature of glands within the body. While each gland may not be secreting the same substance, as long as there is an exocrine function to the cell, it is considered glandular and its malignant form is therefore named adenocarcinoma. Malignant adenocarcinomas invade other tissues and often metastasize given enough time to do so. Ovarian adenocarcinoma is the most common type of ovarian carcinoma. It includes the serous and mucinous adenocarcinomas, the clear cell adenocarcinoma and the endometrioid adenocarcinoma.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e., a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

The cells of a secondary or metastatic tumor are like those in the original tumor. This means, for example, that, if breast cancer metastasizes to the liver, the secondary tumor is made up of abnormal breast cells, not of abnormal liver cells. The tumor in the liver is then called metastatic breast cancer, not liver cancer.

The term "circulating tumor cells" or "CTCs" relates to cells that have detached from a primary tumor or tumor metastases and circulate in the bloodstream. CTCs may constitute seeds for subsequent growth of additional tumors (metastasis) in different tissues. Circulating tumor cells are found in frequencies in the order of 1-10 CTC per mL of whole blood in patients with metastatic disease. Research methods have been developed to isolate CTC. Several research methods have been described in the art to isolate CTCs, e.g., techniques which use of the fact that epithelial cells commonly express the cell adhesion protein EpCAM, which is absent in normal blood cells. Immunomagnetic bead-based capture involves treating blood specimens with antibody to EpCAM that has been conjugated with magnetic particles, followed by separation of tagged cells in a magnetic field. Isolated cells are then stained with antibody to another epithelial marker, cytokeratin, as well as a common leukocyte marker CD45, so as to distinguish rare CTCs from contaminating white blood cells. This robust and semi-automated approach identifies CTCs with an average yield of approximately 1 CTC/mL and a purity of 0.1% (Allard et al., 2004, Clin Cancer Res 10:6897-6904). A second method for isolating CTCs uses a microfluidic-based CTC capture device which involves flowing whole blood through a chamber embedded with 80,000 microposts that have been rendered functional by coating with antibody to EpCAM. CTCs are then stained with secondary antibodies against either cytokeratin or tissue specific markers, such as PSA in prostate cancer or HER2 in breast cancer and are visualized by automated scanning of microposts in multiple planes along three dimensional coordinates. CTC-chips are able to identifying cytokerating-positive circulating tumor cells in patients with a median yield of 50 cells/ml and purity ranging from 1-80% (Nagrath et al., 2007, Nature 450:1235-1239). Another possibility for isolating CTCs is using the CellSearch™ Circulating Tumor Cell (CTC) Test from Veridex, LLC (Raritan, N.J.) which captures, identifies, and counts CTCs in a tube of blood. The CellSearch™ system is a U.S. Food and Drug Administration (FDA) approved methodology for enumeration of CTC in whole blood which is based on a combination of immunomagnetic labeling and automated digital microscopy. There are other methods for isolating CTCs described in the literature all of which can be used in conjunction with the present invention.

A relapse or recurrence occurs when a person is affected again by a condition that affected them in the past. For example, if a patient has suffered from a tumor disease, has received a successful treatment of said disease and again develops said disease said newly developed disease may be considered as relapse or recurrence. However, according to the invention, a relapse or recurrence of a tumor disease may but does not necessarily occur at the site of the original tumor disease. Thus, for example, if a patient has suffered from breast tumor and has received a successful treatment a relapse or recurrence may be the occurrence of a breast tumor or the occurrence of a tumor at a site different to breast. A relapse or recurrence of a tumor also includes situations wherein a tumor occurs at a site different to the site of the original tumor as well as at the site of the original tumor. Preferably, the original tumor for which the patient has received a treatment is a primary tumor and the tumor at a site different to the site of the original tumor is a secondary or metastatic tumor.

By "treat" is meant to administer a compound or composition as described herein to a subject in order to prevent or eliminate a disease, such as an infectious disease and also includes reducing the size of a tumor or the number of tumors in a subject; arrest or slow a disease in a subject; inhibit or slow the development of a new disease in a subject; decrease the frequency or severity of symptoms and/or recurrences in a subject who currently has or who previously has had a disease; and/or prolong, i.e., increase the lifespan of the subject. In particular, the term "treatment of a disease" includes curing, shortening the duration, ameliorating, preventing, slowing down or inhibiting progression or worsening, or preventing or delaying the onset of a disease or the symptoms thereof.

By "being at risk" is meant a subject, i.e., a patient, that is identified as having a higher than normal chance of developing a disease, in particular cancer, compared to the general population. In addition, a subject who has had, or who currently has, a disease, in particular cancer, is a subject who has an increased risk for developing a disease, as such a subject may continue to develop a disease. Subjects who currently have, or who have had, a cancer also have an increased risk for cancer metastases.

In the context of the present invention, terms such as "protect", "prevent", "prophylactic", "preventive", or "protective" relate to the prevention or treatment or both of the occurrence and/or the propagation of a disease in a subject and, in particular, to minimizing the chance that a subject will develop a disease or to delaying the development of a disease. For example, a person at risk for a tumor, as described above, would be a candidate for therapy to prevent a tumor.

According to an embodiment of the present invention, one the subject has been determined to have an infectious disease or other disease state, the subject can be administered an appropriate therapy to treat the infectious disease or other disease state. These therapies, including antibiotics and anti-cancer agents, are well known in the art, and which appropriate therapy ultimately will be given to the subject will be determined by the treating physician.

In an embodiment, the present invention is directed also to a device for carrying out the method according to the present invention, wherein comparing sequence reads with one or more databases comprising the genetic information from a control subject of the same species and the genetic information from a plurality of microorganisms to determine whether or not a compared sequence read maps to a species comprised within the one or more databases is computed by a central processing unit of the device. In an embodiment, the present invention is directed also to a device for carrying out the method according to the present invention, wherein determining over time the number of compared sequence reads mapping to a particular microorganism and the number of compared sequence reads mapping to a species is computed by a central processing unit of the device. In an embodiment, the present invention is directed also to a device for carrying out the method according to the present invention, wherein a significance score for the probability of finding in the subject a compared sequence read mapping to the particular microorganism based on the number of compared sequence reads mapping to the particular microorganism and the number of compared sequence reads mapping to a species is computed by a central processing unit of the device. In an embodiment, the central processing unit is a field-programmable gate array (FPGA). In a preferred embodiment, the device carries out one or more or all of the foregoing computations. In an embodiment, the present invention is directed also to a device that can carry out one or more or all of the computations associated with determining the presence of a disease state in a subject.

Accordingly, the present invention provides a complete diagnostic workflow for the determination of the presence of microorganisms or a disease state in a biological sample based on unbiased sequence analysis of nucleic acids, for example, free circulating DNA. The method advantageously provides a data-driven diagnosis without knowing the suspected microorganism or disease state, does not require specific primer design, and provides the opportunity to detect multiple viral, bacterial, fungal and parasitic microorganism in a single assay.

The method of the present invention is preferably not restricted to the determination of a specific microorganism. In one embodiment, the present method determines the presence of all microorganisms, preferably all microorganisms relevant for a disease state in the subject, such as an infection. The method of the present invention also is preferably not restricted to the determination of a specific type of cancer in a subject, but rather can determine the presence of more than one type of cancer, as well as sub-types of a cancer. In a preferred embodiment, the different types and/or sub-types of cancer in a subject have different mutations in their genetic material, such that the presence in a subject of one or more types and/or sub-types of cancer can be determined in accordance with the methods of the present invention.

Thus, the present invention provides a useful method for identification of the cause of an infection or other disease state in a subject within short time, such that an appropriate therapy for the identified infection or other disease state can be selected within short time.

Accordingly, the method of the present invention can be highly useful for data-driven identification of microorganisms in clinical specimens, for monitoring the microorganism load of a subject and the response to targeted treatment and complement standard clinical microbiology. The method of the present invention also can be highly useful for data-driven identification of the presence of tumor cells in clinical specimens, for monitoring the tumor cell load of a subject and the response to targeted treatment and complement standard clinical oncology.

The present invention is described in detail by the figures and examples below, which are used only for illustration purposes and are not meant to be limiting. Owing to the description and the examples, further embodiments which are likewise included in the invention are accessible to the skilled worker.

FIGURES

EXAMPLES

Figure 1:
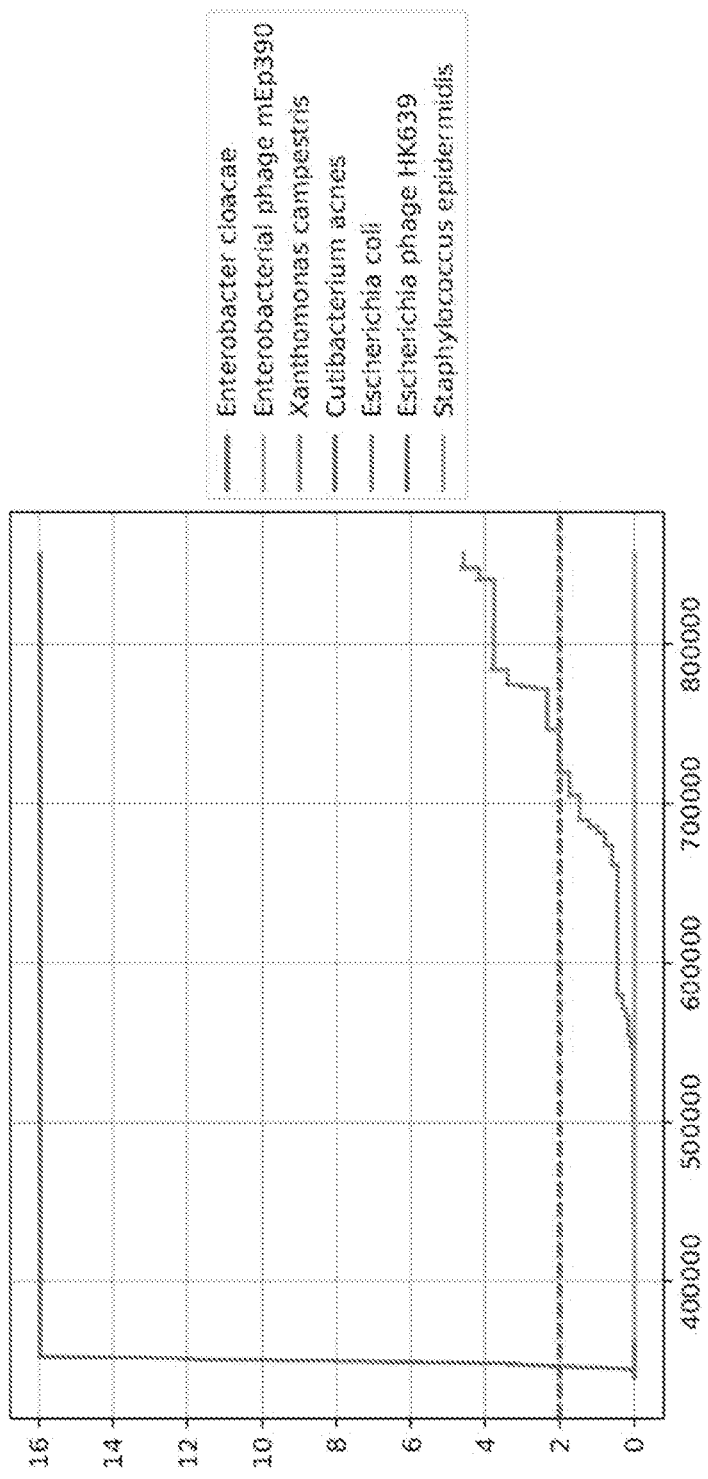
FIG. 1 shows the complete test run for patient S9 (test was not stopped for microorganism being labelled as significant) for seven different microorganisms. A horizontal dashed line is also drawn indicating the statistical relevance threshold.

The techniques and methods used herein are described herein or carried out in a manner known per se and as described, for example, in Sambrook et al., Molecular Cloning: A Laboratory Manual, $2^{nd}$ Edition (1989) Cold Spring Harbor Laboratory Press, Cold Spring Harbor, N.Y. All methods including the use of kits and reagents are carried out according to the manufacturers' information unless specifically indicated.

Example 1

Biological samples, i.e., blood plasma, were obtained from human subjects suspected of suffering from an infectious disease. The nucleic acids in the samples were sequenced using a next-generation sequence method, generating a plurality of sequence reads. This data was stored and subsequently analyzed as follows.

The individual sequence reads were compared to one or more databases comprising the genetic information of both humans and a plurality of microorganisms, such that each read, if possible, was mapped either to a particular microorganism or to the human genome. The mapping provided the total number of reads mapping to a particular microorganism and the total number of reads that could be mapped to a species, i.e., the particular microorganism, the human genome, as well as any other microorganisms, in real time. Thus, the number of reads attributed to a particular microorganism or to the human subject were known at every time point during the diagnostic procedure.

This information allowed for the generation of a count-vector C: $c_m, \ldots, c_l$; m=1, . . . l which holds the number of reads for every species m in a sample/patient j at an arbitrary but fixed point in time during diagnosis. $c_m$ changes over time during the diagnosis of a patient j while new reads are mapped to a species. In addition, C can grow as new microorganism species are identified. At first, an empty vector is initialized and dynamic one is generated during the runtime of the method. C describes the microbial burden of the patient currently diagnosed. To identify those microbes which burden is of abnormal abundance, the inverse cumulative density function (cdf) of this specific microbial burden in patient j at a given time was calculated as follows:

$$p(M_j) = 1 - cdf(c_m; n, p_M) = 1 - \sum_{i=0}^{c_m} \binom{n}{i} p_m^i (1 - p_m)^{n-i} \quad [1]$$

where $c_m$ is the number of reads measured for species m in patient j at the current time and n the number of reads which are able to be mapped in total (microbial and host). $p_M$ describes the discovery probability which is calculated in real time and represents the probability to detect a read for species m.

In contrast to conventional testing, this is not an endpoint test but is running in the framework of sequential testing. Thus, through the sequential testing approach all necessary and important information is available while the test runs and not after the test finishes. This provides a new way of infection diagnosis and a new way of testing procedures in the area of next generation sequencing. The information provided is a p-value which describes whether or not the current amount of nucleic acid mapped to a certain species is considered unusual and therefore reaches a very low p-value given the discovery probability for this species and the current running test setup.

This method allows for the definition of new characteristic variables such as "microbial signals per event". These variables are directly dependent on the times a microorganism becomes statistically relevant and therefore the new variables are of particular importance. Possible characteristic variables are "microbial reads per second" or "microbial reads per human reads". For every subject and every microorganism such variables can be calculated and therefore will provide a deeper insight into the degree of severity of infection for each sample analyzed. In addition those characteristic variables will enable the comparison of samples sequenced with different technologies because of the technological independence of such variables.

Example 2

Nucleic acids from a biological sample of blood plasma obtained from subject S9 were sequenced such that the probability of finding in the subject a compared sequence read mapping to the particular microorganism based on the number of compared sequence reads mapping to the particular microorganism and the number of compared sequence reads mapping to a species was calculated according to the invention. The results are presented in FIG. 1.

FIG. 1 shows the complete test sequence (the test was not interrupted or aborted by significance for certain microorganisms) for 7 different microorganisms at the same time. A horizontal red-dashed line is also shown which represents a statistical threshold which must be exceeded before a microorganism is considered "relevant" for causing the infection. It is also clear that the blue line, representing the microorganism *Enterobacter cloacae*, exceeded the statistical threshold only after a few moments of generating data such that the test could have been terminated after only a few moments for this microorganism. The purple line, belonging to the bacterium *E. coli*, shows a slow increase in value but does not cross the significance level as being relevant until after 500 k reads, indicating that it and the other microorganisms are either contamination or commensal microorganisms.

Example 3

Nucleic acids from a biological sample of blood plasma obtained from subject S11 were sequenced such that the probability of finding in the subject a compared sequence read mapping to the particular microorganism based on the number of compared sequence reads mapping to the particular microorganism and the number of compared sequence reads mapping to a species was calculated according to the present invention. The results are presented in FIG. 2.

Figure 2:
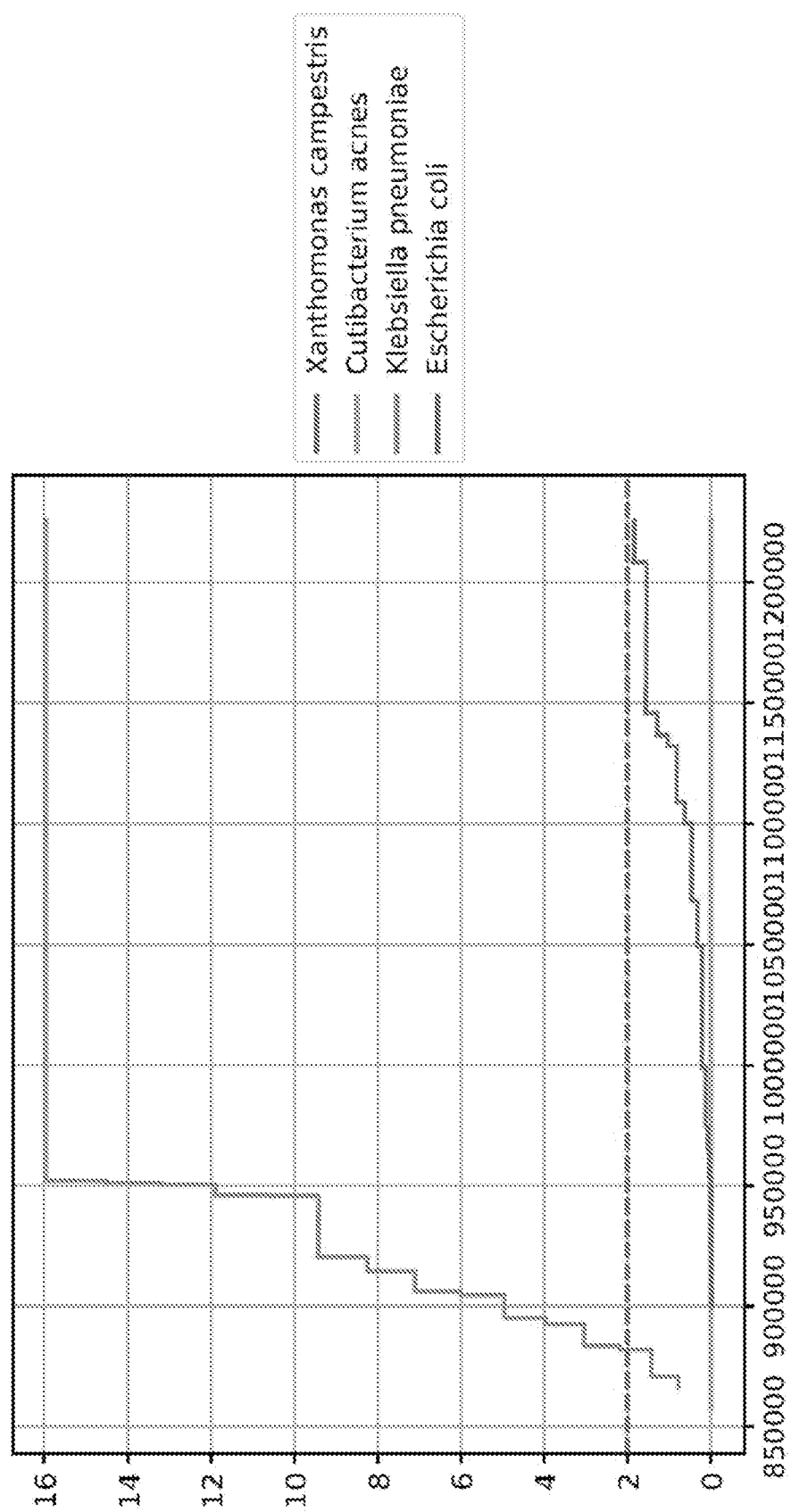
FIG. 2 shows the complete test run for patient S11 (test was not stopped for microorganism being labelled as significant) for four different microorganisms. A horizontal dashed line is also drawn indicating the statistical relevance threshold.

Similarly to FIG. 1, FIG. 2 shows a fast rise in the probability of a single bacterium, here *K. pneumoniae* (in green), is relevant to the disease state, i.e., the causative agent of the infection. It is noted that *Cutibacterium acnes*, which is a bacterium living on human skin is detected but the relevance/probability for this bacterium to be the causative agent of the infection is zero. This indicates that the method, as intended, filters out commensal species. In contrast, the relevance of *E. coli* increases up to the significance threshold over a time frame of 350 k reads. Although it is not shown as relevant this might indicate that the patient is in danger of developing a secondary infection caused by *E. coli*.

This indicates that the method generates information that a current "endpoint based" test may not be able to provide. Thus, this method provides data that indicates to the clinician to act against an infection before it is actually clinically relevant. Another advantage of the herein described method is the ability to detect infections caused by multiple microorganisms, and to further break down which microorganisms are the main causative agent(s).

Example 4

Nucleic acids from a biological sample of blood plasma obtained from subject S60 were sequenced such that the probability of finding in the subject a compared sequence read mapping to the particular microorganism based on the number of compared sequence reads mapping to the particular microorganism and the number of compared sequence reads mapping to a species was calculated according to the present invention. The results are presented in FIG. 3.

Figure 3:
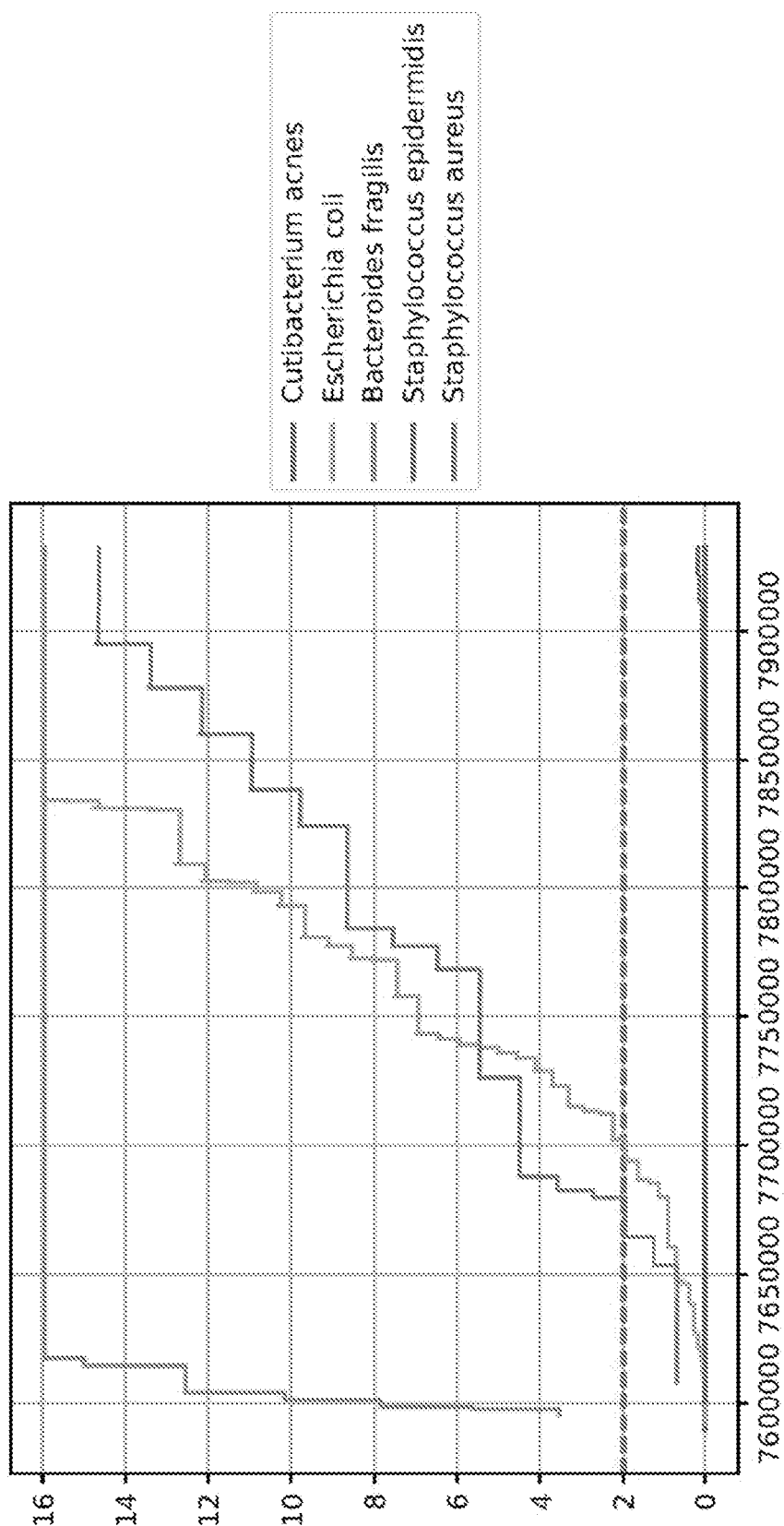
FIG. 3 shows the complete test run for patient S60 (test was not stopped for microorganism being labelled as significant) for five different microorganisms. A horizontal dashed line is also drawn indicating the statistical relevance threshold.

As is clearly depicted in FIG. 3, the main infectious agent is *B. fragilis*, since the green line crosses the relevance threshold right at the start of the method. However, after some events (reads analyzed) two other bacteria make a significant leap over the relevance threshold showing that those two are also contributing to the sepsis of the subject, indicated by the orange and purple line for *E. coli* and *S. aureus*, respectively.

Comparing this result with the traditional outcome based on a routine test for all three bacteria, the results would look the same. Each microorganism would have been assigned more or less the same relevance. However, using the method described herein, the main causative agent was clearly identified, and through the objective use of characteristics variables such as "events per time" the main causative agent as well as other microorganisms contributing to the infection were identified.

The axis in the above the figures is always the logarithm of the p-value calculated with Formula 1 and the number of reads analyzed. Of course, it is possible to alter the units depicted on this axis. Here it is solely necessary that through the new units, a unique ordering of reads is possible. This might be, for example, the order with which reads were generated or the time they were compared to the database. Using the above-described method, the above-mentioned characteristic variables, for example "reads per event until relevant" for a specific microorganism and patient can be calculated. These variables can be used to compare different patients suffering from the same microorganism. Further, the main causative agent can be identified by comparing the variables of different microbes in the very same patient.

It is assumed that real infections range in a certain interval say [x-y] measured, for example, by "reads per event". Contaminants and commensals would then show up outside of the boundaries of this "infection interval". Therefore, statistical analysis using those infection intervals suffices to identify infections and assess the relevance of the identified microorganisms. In addition, the severity of the infection is assessed by those intervals. This is accomplished using the statistical framework of waiting time analysis. Most of the time, waiting times analyses are carried out using an exponential function. Therefore, assuming that a variable describing the "characteristic infection variable" is distributed following the exponential random variable:

$$X \sim Exp(\lambda) \qquad [2]$$

and assuming that the wait time for a certain microorganism is between 500-1000 reads, we have $\lambda = 1/500$ and $\lambda = 1/1000$. Since we are interested in the probability of $P(500 < X < 1000)$, we calculate $P(x<1000) - P(x \leq 500)$. This describes the probability of NOT suffering from an infection. Since we want a faster interval than this, we calculate $P(X \leq 500)$. Now, if the 500th read is again a microorganism read, what we do is calculate $P(X>500) = e^{-500\lambda} \approx 0.36$. So, it is very likely to see a microorganism read after 500 reads of the host given the interval of 500-1000 for this particular species. However, if we see a second microorganism read just after 10 reads, we calculate $P(X>10) = e^{-100\lambda} \approx 0.98$ since we have seen a microorganism read after 10 signals (compared reads) we are interested in $P(X \leq 10)$ and therefore $1 - P(X>10) = 0.019$. Thus, it is highly unlikely to detect a microorganism after 10 signals, so that if a microorganism is detected after 10 signals, there is a need to report it to the clinician.

Both approaches, the coupling of probabilities with a fixed but arbitrary amount of events given a set of events and the resulting waiting time analysis are not described in infectious disease diagnostics or in diagnostics in general. In general, if data generation can be separated into different channels or blocks, we can again parallelize the testing towards each individual channel (i.e., testing every channel individually and treating each channel as a separate experiment) and therefore minimizing the time to result. This, as well, is not possible using endpoint testing, meaning that the method described herein is scalable towards higher throughput in contrast to endpoint based testing.

The invention provides, in particular, the following:

1. A method for determining the presence of microorganisms in a subject comprising:
    (a) sequencing nucleic acids present in a biological sample obtained from the subject to obtain a plurality of nucleic acid sequence reads;
    (b) comparing sequence reads obtained in step (a) with one or more databases comprising the genetic information from a control subject of the same species and the genetic information from a plurality of microorganisms to determine whether or not a compared sequence read maps to a species comprised within the one or more databases; and
    (c) determining over time the number of compared sequence reads mapping to a particular microorganism and the number of compared sequence reads mapping to a species.

2. A method for determining the presence of microorganisms in a subject comprising:
    (a) comparing sequence reads with one or more databases comprising the genetic information from a control subject of the same species and the genetic information from a plurality of microorganisms to determine whether or not a compared sequence read maps to a species comprised within the one or more databases, wherein the sequence reads are obtained by sequencing nucleic acids present in a biological sample obtained from the subject; and
    (b) determining over time the number of compared sequence reads mapping to a particular microorganism and the number of compared sequence reads mapping to a species.

3. The method according to item 1 or 2, wherein the method further comprises computing a significance score for the probability of finding in the subject a compared sequence read mapping to the particular microorganism based on the number of compared sequence reads mapping to the particular microorganism and the number of compared sequence reads mapping to a species.

4. The method according to item 3, wherein when the score for the particular microorganism meets or exceeds a threshold value, the particular microorganism is determined to be present in the subject.

5. The method according to item 3, wherein when the score for the particular microorganism meets or exceeds a threshold value, the particular microorganism is determined to be relevant for causing a disease in the subject.

6. The method according to item 5, wherein when the score for the particular microorganism exceeds a threshold value with few sequence reads, the disease due to the presence of the microorganism is considered to be severe.

7. A method for determining the presence of a disease state in a subject comprising:
    (a) sequencing nucleic acids present in a biological sample obtained from the subject to obtain a plurality of nucleic acid sequence reads;
    (b) comparing sequence reads obtained in step (a) with one or more databases comprising the genetic information from a control subject of the same species to determine whether or not a compared sequence read maps to the control subject; and (c) determining over time the number of compared sequence reads mapping and not mapping to the control subject.

8. The method according to item 7, wherein the method further comprises computing a significance score for the probability of finding in the subject a compared sequence read not mapping to the control subject based on the number of compared sequence reads not mapping to the control subject and the number of compared sequence reads mapping to the control subject.

9. The method according to item 8, wherein when the score meets or exceeds a threshold value, the disease state is determined to be present in the subject.

10. The method according to any one of items 7 to 9, wherein the disease state is cancer.

11. The method according to item 10, wherein the cancer is caused by a genetic abnormality.

12. The method according to any one of items 7 to 9, wherein the disease state is an infection caused by a microorganism.

13. The method according to item 12, wherein the microorganism is a virus, a bacterium, a fungus or a parasite.

14. The method according to any one of the preceding items, wherein the biological sample is selected from the group consisting of whole blood, serum, blood plasma, amniotic fluid, synovial fluid, liquor, tissue or cell smear, tissue or cell swab, urine, tissue, sputum, stool, gastrointestinal secretions, lymph fluid, and lavage.

15. The method according to any one of the preceding items, wherein the subject is a vertebrate, preferably a mammal, for example, human, dog, cat, pig, horse, cattle, sheep, goat, mouse, or rat.

16. The method according to item 15, wherein the subject is human.

17. The method according to any one of the preceding items, wherein the sequencing is performed by molecular high-throughput sequence analysis.

18. The method according to any one of the preceding items, wherein when the particular microorganism or the disease state is determined to be present in the subject, the method further comprises administering to the subject a pharmaceutically-active compound known to treat a disease caused by the particular microorganism or the disease state.

19. A method for diagnosing an infectious disease caused by microorganisms in a subject comprising:

(a) sequencing nucleic acids present in a biological sample obtained from the subject to obtain a plurality of nucleic acid sequence reads;

(b) comparing sequence reads obtained in step (a) with one or more databases comprising the genetic information from a control subject of the same species and the genetic information from a plurality of microorganisms to determine whether or not a compared sequence read maps to a species comprised within the one or more databases;

(c) determining over time the number of compared sequence reads mapping to a particular microorganism and the number of compared sequence reads mapping to a species; and (d) computing a significance score for the probability of finding in the subject a compared sequence read mapping to the particular microorganism based on the number of compared sequence reads mapping to the particular microorganism and the number of compared sequence reads mapping to a species, wherein when the score for the particular microorganism meets or exceeds a threshold value, the particular microorganism is determined to be causing the infectious disease.

20. A computer-readable storage medium storing program code comprising instructions which when executed by a processor carry out the method according to any one of items 1 to 19.

21. A computer system comprising a processor configured to carry out the method according to any one of items 1 to 19.

What is claimed:

1. A method of treating a disease or infection caused by a microorganism in a subject comprising administering to the subject a compound that inhibits the growth of a microorganism whose significance score meets or exceeds a threshold value, wherein the significance score is calculated by:

comparing sequence reads with one or more databases comprising the genetic information from a control subject of the same species and the genetic information from a plurality of microorganisms to determine whether or not a compared sequence read maps to a species comprised within the one or more databases, wherein the sequence reads are obtained by sequencing nucleic acids present in a biological sample obtained from the subject;

determining over time the number of compared sequence reads mapping to a particular microorganism and the number of compared sequence reads mapping to a species, wherein the sequence reads mapping to a species comprise sequence reads mapping to the species of the subject; and computing a significance score for the probability of finding in the subject a compared sequence read mapping to the particular microorganism based on the number of compared sequence reads mapping to the particular microorganism and the number of compared sequence reads mapping to a species.

2. The method according to claim 1, wherein when the significance score for the particular microorganism meets or exceeds a threshold value, the particular microorganism is determined to be present in the subject.

3. The method according to claim 1, wherein when the significance score for the particular microorganism meets or exceeds a threshold value, the particular microorganism is determined to be relevant for causing a disease in the subject.

4. The method according to claim 3, wherein when the significance score for the particular microorganism exceeds a threshold value with few sequence reads, the disease due to the presence of the microorganism is considered to be severe.

5. A method of treating a disease or infection caused by a microorganism in a subject comprising administering to the subject a compound that inhibits the growth of a microorganism whose significance score meets or exceeds a threshold value, wherein the significance score is calculated by:

computing over time a significance score for the probability of finding in the subject a sequence read mapping to a particular microorganism based on the number of sequence reads mapping to the particular microorganism and the number of sequence reads mapping to a species, wherein the sequence reads mapping to a species comprise sequence reads mapping to the species of the subject;

wherein the sequence reads mapping to the particular microorganism and the sequence reads mapping to a species are obtained by comparing sequence reads with one or more databases comprising the genetic information from a control subject of the same species and the genetic information from a plurality of microorganisms to determine whether or not a compared sequence read maps to a species comprised within the one or more databases, and wherein the sequence reads are generated by sequencing nucleic acids present in a biological sample obtained from the subject.

6. The method according to claim 5, wherein when the significance score for the particular microorganism meets or exceeds a threshold value, the particular microorganism is determined to be present in the subject.

7. The method according to claim 5, wherein when the significance score for the particular microorganism meets or exceeds a threshold value, the particular microorganism is determined to be relevant for causing a disease in the subject.

8. The method according to claim 7, wherein when the significance score for the particular microorganism exceeds a threshold value with few sequence reads, the disease due to the presence of the microorganism is considered to be severe.

9. A method of treating a disease or infection caused by a microorganism in a subject comprising administering to the subject a compound that inhibits the growth of a microorganism whose significance score meets or exceeds a threshold value, wherein the significance score is calculated by:

determining over time the number of sequence reads mapping to a particular microorganism and the number of sequence reads mapping to a species, wherein the sequence reads mapping to a species comprise sequence reads mapping to the species of the subject; wherein the sequence reads are obtained by comparing sequence reads with one or more databases comprising the genetic information from a control subject of the same species and the genetic information from a plurality of microorganisms to determine whether or not a sequence read maps to a species comprised within the one or more databases, and wherein the sequence reads are generated by sequencing nucleic acids present in a biological sample obtained from the subject; and computing a significance score for the probability of finding in the subject a sequence read mapping to the particular microorganism based on the number of sequence reads mapping to the particular microorganism and the number of sequence reads mapping to a species.

10. The method according to claim 9, wherein when the significance score for the particular microorganism meets or exceeds a threshold value, the particular microorganism is determined to be present in the subject.

11. The method according to claim 9, wherein when the significance score for the particular microorganism meets or exceeds a threshold value, the particular microorganism is determined to be relevant for causing a disease in the subject.

12. The method according to claim 11, wherein when the significance score for the particular microorganism exceeds a threshold value with few sequence reads, the disease due to the presence of the microorganism is considered to be severe.

13. The method according to claim 9, wherein the sequence reads mapping to a species further comprise sequence reads mapping to any other microorganism present in the sample.

14. The method according to claim 1, wherein the sequence reads mapping to a species further comprise sequence reads mapping to any other microorganism present in the sample.

15. The method according to claim 5, wherein the sequence reads mapping to a species further comprise sequence reads mapping to any other microorganism present in the sample.

* * * * *